United States Patent [19]

Maraganore

[11] Patent Number: 5,446,131
[45] Date of Patent: Aug. 29, 1995

[54] THROMBIN RECEPTOR ANTAGONISTS

[75] Inventor: John M. Maraganore, Concord, Mass.

[73] Assignee: Biogen, Inc., Cambridge, Mass.

[21] Appl. No.: 328,388

[22] Filed: Oct. 24, 1994

Related U.S. Application Data

[63] Continuation of Ser. No. 847,561, Mar. 2, 1992, abandoned.

[51] Int. Cl.$^6$ .......................... C07K 7/00; C07K 7/08; A61K 38/00
[52] U.S. Cl. ................................................. 530/326
[58] Field of Search ........................... 514/13; 530/326

[56] References Cited

U.S. PATENT DOCUMENTS

| | | | |
|---|---|---|---|
| 4,859,609 | 8/1989 | Dull et al. | 436/501 |
| 5,049,132 | 9/1991 | Shaffer et al. | 604/101 |
| 5,071,954 | 12/1991 | Felzer et al. | 530/324 |

FOREIGN PATENT DOCUMENTS

| | | | |
|---|---|---|---|
| 0220157 | 4/1987 | European Pat. Off. | C07K 7/08 |
| 372670 | 6/1990 | European Pat. Off. | A61K 37/02 |
| WO88/03151 | 5/1988 | WIPO | C07K 7/00 |
| 9214750 | 3/1992 | WIPO | |
| WO92/14750 | 9/1992 | WIPO | |

OTHER PUBLICATIONS

E. M. Ruda et al., "Identification of a Tripeptide Analogue (SC–40476) That Acts as a Selective Partial Agonist–Antagonist at the Human Platelet Thrombin Receptor", *Ann. New York Acad. Sci.*, 485, pp. 439–442 (1986).

E. M. Ruda et al., "Thrombin Receptor Antagonists—Structure-Activity Relationships for the Platelet Thrombin Receptor and Effects on Prostacyclin Synthesis by Human Umbilican Vein Endothelial Cells", *Biochem. Pharm.*, 39, pp. 373–381 (1990).

S. J. Friezner Degen et al., "Nucleotide Sequence of the Gene for Human Prothrombin", *Biochemistry*, 26, pp. 6165–6177 (1987).

G. Noe et al., "The Use of Sequence-specific Antibodies to Identify a Secondary Binding Site in Thrombin", *J. Biol. Chem.*, 263, pp. 11729–11735 (1988).

W. Bode et al., "The Refined 1.9 Å Crystal Structure of Human α-Thrombin: Interaction With D-Phe-Pro-Arg chloromethylketone and Significance of the Tyr-Pro-Pro-Trp Insertion Segment", *EMBO J.*, 8, pp. 3467–3475 (1989).

(List continued on next page.)

*Primary Examiner*—Jill Warden
*Assistant Examiner*—S. G. Marshall
*Attorney, Agent, or Firm*—Fish & Neave; James F. Haley, Jr.; Andrew S. Marks

[57] ABSTRACT

This invention relates to novel, biologically active molecules which bind to and inhibit the thrombin receptor. These thrombin receptor antagonists are further characterized by their ability to inhibit thrombin-induced platelet aggregation and their inability to inhibit platelet aggregation induced by an internal peptide fragment of the platelet thrombin receptor. More specifically, the thrombin receptor antagonist of this invention comprises the formula: $A_1\text{-}X\text{-}X\text{-}X\text{-}A_2\text{-}X\text{-}A_3\text{-}X\text{-}A_4\text{-}B\text{-}X\text{-}A_5\text{-}C\text{-}X\text{-}A_6$; wherein each of $A_1$ and $A_6$, either the same or different, are selected from the group consisting of a positively charged amino acid and an acyl or alkyl chain comprising from 1 to 10 backbone atoms and a positively charged side group; each of $A_2$, $A_3$, $A_4$ and $A_5$, is a positively charged amino acid, either the same or different; each X is any amino acid, either the same or different; B is an amino acid containing an aryl side chain; and C is a polar amino acid. This invention also relates to compositions and methods which employ these molecules for therapeutic and prophylactic purposes.

14 Claims, 4 Drawing Sheets

OTHER PUBLICATIONS

A. J. B. Brady et al., "Angioplasty and Restenosis", *Brit. Med. J.*, 303, pp. 729–730 (Sep. 1991).

M. O. Dayhoff et al., "A Model of Evolutionary Change in Proteins" in *Atlas of Protein Sequence and Structure No. 5*, M. O. Dayhoff, ed., National Biomedical Research Foundation, Wash., D.C., 89–100 (1978).

J. W. Fenton, II, "Thrombin Bioregulatory Functions", *Adv. Clin. Enzymol.*, 6, pp. 186–193 (1988).

D. Gurwitz et al., "Thrombin Modulates and Reverses Neuroblastoma Neurite Outgrowth", *Proc. Natl. Acad. Sci. USA*, 85, pp. 3440–3444 (1988).

R.-S. Huang et al., "Thrombin' Receptor-directed Ligand Accounts for Activation by Thrombin of Platelet Phospholipase C and Accumulation of 3-Phosphorylated Phosphoinositides", *J. Biol. Chem.*, 266, pp. 18435–18438 (Oct. 1991).

D. T. Hung et al., "Thrombion-induced Events in Non-Platelet Cells Are Mediated by the Unique Proteolytic Mechanism Established for the Cloned Platelet Thrombin Receptor", *J. Cell Biol.*, 116, pp. 827–832 (Feb. 1992).

L.-W. Liu et al., "The Region of the Thrombin Receptor Resembling Hirudin Binds to Thrombin and Alters Enzyme Specificity", *J. Biol. Chem.*, 266, pp. 16977–16980 (Sep. 1991).

S. Prescott et al., "Human Endothelial Cells in Culture Produce Platelet-Activating Factor (1-alkyl-2-acetyl-sn-glycero-3-phosphocholine). When Stimulated With Thrombin", *Proc. Natl. Acad. Sci. USA*, 81, pp. 3534–3538 (1984).

E. Skrzypczak-Jankun et al., "Structure of the Hirugen and Hirulog 1 Complexes of α-Thrombin", *J. Mol. Biol.*, 221, pp. 1379–1393 (1991).

D. N. Tatakis et al., "Thrombin Effects On Osteoblastic Cells -II. Structure-Function Relationships", *Biochem. Biophys. Res. Comm.*, 174, pp. 181–188 (Jan. 1991).

T.-K. H. Vu et al., "Molecular Cloning of a Functional Thrombin Receptor Reveals a Novel Proteolytic Mechanism of Receptor Activation", *Cell*, 64, pp. 1057–1068 (Mar. 22, 1991).

T.-K. H. Vu et al., "Domains Specifying Thrombin-Receptor Interaction", *Nature*, 353, pp. 674–677 (Oct. 1991).

J. N. Wilcox, "Thrombin and Other Potential Mechanisms Underlying Restenosis", *Circulation*, 84, pp. 432–435 (Jul. 1991).

Wolinsky et al., "Use of a Perforated Balloon Catheter to Deliver Concentrated Heparin Into the Wall of the Normal Canine Artery", *J. Amer. Coll. Cardiol.*, 15, pp. 475–481 (Feb. 1990).

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
            ( A ) NAME/KEY: Binding-site
            ( B ) LOCATION: 1..20
            ( D ) OTHER INFORMATION: /label=anion binding
                    / note="corresponds to amino acids 65-83 of
                    thrombin"

( x i ) SEQUENCE DESCRIPTION: SEQ ID NO:1:

Leu Val Arg Ile Gly Lys His Ser Arg Thr Arg Tyr Glu Arg Asn Ile
    1               5                   10                  15

Glu Lys Ile Ser
                20

( 2 ) INFORMATION FOR SEQ ID NO:2:

( i ) SEQUENCE CHARACTERISTICS:
            ( A ) LENGTH: 14 amino acids
            ( B ) TYPE: amino acid
            ( D ) TOPOLOGY: linear ( i i ) MOLECULE TYPE: peptide ( i i i ) HYPOTHETICAL: NO ( v ) FRAGMENT TYPE: internal ( i x ) FEATURE:
            ( A ) NAME/KEY: Peptide
            ( B ) LOCATION: 1..14
            ( D ) OTHER INFORMATION: /label=tethered ligand
                    / note="amino acids 42-55 of the platelet surface
                    thrombin receptor"

( x i ) SEQUENCE DESCRIPTION: SEQ ID NO:2:

Ser Phe Leu Leu Arg Asn Pro Asn Asp Lys Tyr Glu Pro Phe
    1               5                   10

( 2 ) INFORMATION FOR SEQ ID NO:3:

( i ) SEQUENCE CHARACTERISTICS:
            ( A ) LENGTH: 17 amino acids
            ( B ) TYPE: amino acid
            ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

Leu Val Arg Ile Gly Lys His Ser Arg Thr Arg Tyr Glu Arg Asn Ile
    1               5                   10                  15

Glu ( 2 ) INFORMATION FOR SEQ ID NO:4:

( i ) SEQUENCE CHARACTERISTICS:
            ( A ) LENGTH: 16 amino acids
            ( B ) TYPE: amino acid
            ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Leu Cys Arg Ile Gly Lys His Ser Arg Thr Arg Tyr Glu Arg Asn Ile
    1               5                   10                  15

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

```
Leu Val Arg Ile Gly Lys His Ser Arg Thr Arg Tyr Glu Arg Asn Ile
1               5                   10                  15
Glu Lys Ile
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 6..7
        ( D ) OTHER INFORMATION: /label=modified aa
            / note="residue 6 is Orn"

( x i ) SEQUENCE DESCRIPTION: SEQ ID NO:6:

```
Leu Val Arg Ile Gly Arg His Ser Arg Thr Arg Tyr Glu Arg Asn Ile
1               5                   10                  15
Glu Lys Ile
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

```
Leu Val Arg Ile Gly Lys His Ser Arg Thr Arg Tyr Asp Arg Asn Ile
1               5                   10                  15
Glu Lys Ile
```

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 3..4
        ( D ) OTHER INFORMATION: /label=modified aa
            / note="Xaa is beta-homoarginine"

( x i ) SEQUENCE DESCRIPTION: SEQ ID NO:8:

```
        Leu Val Xaa Ile Gly Lys His Ser Arg Thr Arg Tyr Glu Arg Asn Ile
        1               5                   10                  15

Glu Lys Ile
```

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 19..20
        ( D ) OTHER INFORMATION: /label=modified aa
            / note="Xaa is cyclohexylalanine (Cha)"

( x i ) SEQUENCE DESCRIPTION: SEQ ID NO:9:

```
        Leu Val Arg Ile Gly Lys His Ser Arg Thr Arg Tyr Glu Arg Asn Ile
        1               5                   10                  15

Glu Lys Xaa Gly
                    20
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: circular ( i i ) MOLECULE TYPE: peptide ( i i i ) HYPOTHETICAL: NO ( i x ) FEATURE:
        ( A ) NAME/KEY: Modified-site
        ( B ) LOCATION: 1..2
        ( D ) OTHER INFORMATION: /label=N- terminus
            / note="Xaa is an N-terminal mercaptopropionic
            acid (MPR)."

( i x ) FEATURE:
        ( A ) NAME/KEY: Disulfide-bond
        ( B ) LOCATION: 1..19
        ( D ) OTHER INFORMATION: /label=cyclic peptide
            / note="the N-terminal mercaptopropionic acid
            residue is disulfide bonded to the C-terminal
            cysteine residue, creating a cyclic peptide."

( x i ) SEQUENCE DESCRIPTION: SEQ ID NO:10:

```
        Xaa Val Arg Ile Gly Lys His Ser Arg Thr Arg Tyr Glu Arg Asn Ile
        1               5                   10                  15

Glu Lys Cys
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: circular ( i i ) MOLECULE TYPE: peptide ( i i i ) HYPOTHETICAL: NO ( i x ) FEATURE:
        ( A ) NAME/KEY: Modified-site
        ( B ) LOCATION: 1..2
        ( D ) OTHER INFORMATION: /label=N- terminus
            / note="Xaa at residue 1 is mercaptopropionic acid ( M P R )"

( i x ) FEATURE:
    ( A ) NAME/KEY: Modified-site
    ( B ) LOCATION: 2..3
    ( D ) OTHER INFORMATION: /label=modified aa
        / note="Xaa at residue 2 is cyclohexylalanine
( C h a )"

( i x ) FEATURE:
    ( A ) NAME/KEY: Disulfide-bond
    ( B ) LOCATION: 1..20
    ( D ) OTHER INFORMATION: /label=cyclic peptide
        / note="The N-terminal mercaptopropionic acid
        residue is disulfide bonded to the C-terminal
        cysteine residue, creating a cyclic peptide."

( x i ) SEQUENCE DESCRIPTION: SEQ ID NO:11:

```
Xaa Xaa Val Arg Ile Gly Lys His Ser Arg Thr Arg Tyr Glu Arg Asn
1               5                   10                      15

Ile Glu Lys Cys
            20
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 10..11
        ( D ) OTHER INFORMATION: /label=modified aa
            / note="Xaa is cyclohexylalanine (Cha)"

( x i ) SEQUENCE DESCRIPTION: SEQ ID NO:12:

```
Leu Val Arg Ile Gly Lys His Ser Arg Xaa Arg Tyr Glu Arg Asn Ile
1               5                   10                      15

Glu Lys Ile
```

( 2 ) INFORMATION FOR SEQ ID NO:13:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 12..13
        ( D ) OTHER INFORMATION: /label=modified aa
            / note="The tyrosine at residue 12 is diiodinated
            at the 3 and 5 positions of the ring."

( x i ) SEQUENCE DESCRIPTION: SEQ ID NO:13:

```
Leu Val Arg Ile Gly Lys His Ser Arg Thr Arg Tyr Glu Arg Asn Ile
1               5                   10                      15

Glu Lys Ile
```

( 2 ) INFORMATION FOR SEQ ID NO:14:

( i ) SEQUENCE CHARACTERISTICS:
        ( A ) LENGTH: 17 amino acids
        ( B ) TYPE: amino acid (D) TOPOLOGY: linear (ii) MOLECULE TYPE: peptide (iii) HYPOTHETICAL: NO (ix) FEATURE:
    (A) NAME/KEY: Modified-site
    (B) LOCATION: 1..2
    (D) OTHER INFORMATION: /label=N- terminus
    / note="Xaa is guanidinobenzoic acid"

(xi) SEQUENCE DESCRIPTION: SEQ ID NO:14:

Xaa Ile Gly Lys His Ser Arg Thr Arg Tyr Glu Arg Asn Ile Glu Lys
1                   5                   10                  15

Ile (2) INFORMATION FOR SEQ ID NO:15:

(i) SEQUENCE CHARACTERISTICS:
    (A) LENGTH: 15 amino acids
    (B) TYPE: amino acid
    (D) TOPOLOGY: both (ii) MOLECULE TYPE: peptide (ix) FEATURE:
    (A) NAME/KEY: Modified-site
    (B) LOCATION: one-of(1, 5, 7, 9, 12, 15)
    (D) OTHER INFORMATION: /note="positively charged amino
    acid"

(ix) FEATURE:
    (A) NAME/KEY: Modified-site
    (B) LOCATION: one-of(2, 3, 4, 6, 8, 11, 14)
    (D) OTHER INFORMATION: /note="any amino acid"

(ix) FEATURE:
    (A) NAME/KEY: Modified-site
    (B) LOCATION: 10
    (D) OTHER INFORMATION: /note="amino acid containing an
    aryl side chain"

(ix) FEATURE:
    (A) NAME/KEY: Modified-site
    (B) LOCATION: 13
    (D) OTHER INFORMATION: /note="polar amino acid"

(xi) SEQUENCE DESCRIPTION: SEQ ID NO:15:

Xaa Xaa Xaa Xaa Xaa Xaa Xaa Xaa Xaa Xaa Xaa Xaa Xaa Xaa Xaa
1                   5                   10                  15

(2) INFORMATION FOR SEQ ID NO:16:

(i) SEQUENCE CHARACTERISTICS:
    (A) LENGTH: 17 amino acids
    (B) TYPE: amino acid
    (D) TOPOLOGY: both (ii) MOLECULE TYPE: peptide (ix) FEATURE:
    (A) NAME/KEY: Modified-site
    (B) LOCATION: one-of(1, 5, 7, 9, 12, 15, 16)
    (D) OTHER INFORMATION: /note="positively charged amino
    acid"

(ix) FEATURE:
    (A) NAME/KEY: Modified-site
    (B) LOCATION: one-of(2, 3, 4, 6, 8, 11, 14)
    (D) OTHER INFORMATION: /note="any amino acid"

(ix) FEATURE:
    (A) NAME/KEY: Modified-site
    (B) LOCATION: 10
    (D) OTHER INFORMATION: /note="amino acid containing an
    aryl side chain"

(ix) FEATURE:
    (A) NAME/KEY: Modified-site
    (B) LOCATION: 13
    (D) OTHER INFORMATION: /note="polar amino acid"

(ix) FEATURE:
    (A) NAME/KEY: Modified-site
    (B) LOCATION: 17
    (D) OTHER INFORMATION: /note="hydrophobic amino acid"

(xi) SEQUENCE DESCRIPTION: SEQ ID NO:16:

Xaa Xaa Xaa Xaa Xaa Xaa Xaa Xaa Xaa Xaa Xaa Xaa Xaa Xaa Xaa Xaa
1               5                   10                  15

Xaa

THROMBIN RECEPTOR ANTAGONISTS

This is a continuation of application Ser. No. 847,561, filed Mar. 2, 1992 and now abandoned, entitled THROMBIN RECEPTOR ANTAGONISTS.

TECHNICAL FIELD OF THE INVENTION

This invention relates to novel, biologically active molecules which bind to and inhibit the thrombin receptor. The molecules of this invention are characterized by a portion which binds to the "hirundin-like" domain of the thrombin receptor (amino acids 52-69). These thrombin receptor antagonists are further characterized by their ability to inhibit thrombin-induced platelet aggregation and their inability to inhibit platelet aggregation induced by an internal peptide fragment of the platelet thrombin receptor. More specifically the thrombin receptor antagonist of this invention comprises the formula: SEQ ID NO: 15: $A_1$-X-X-X-$A_2$-X-$A_3$-X-$A_4$-B-X-$A_5$-C-X-$A_6$; wherein each of $A_1$ and $A_6$, either the same or different, are selected from the group consisting of a positively charged amino acid and an acyl or alkyl chain comprising from 1 to 10 backbone atoms and a positively charged side group; each of $A_2$, $A_3$, $A_4$ and $A_5$, is a positively charged amino acid, either the same or different; each X is any amino acid, either the same or different; B is an amino acid containing an aryl side chain; and C is a polar amino acid. This invention also relates to compositions and methods which employ these molecules for therapeutic and prophylactic purposes.

BACKGROUND OF THE INVENTION

Thrombin is a naturally occurring protein which has several bioregulatory roles [J. W. Fenton, II, "Thrombin Bioregulatory Functions", *Adv. Clin. Enzymol.*, 6, pp. 186-93 (1988)]. In addition to being intimately involved in blood coagulation, thrombin is also known to play a role in platelet and endothelial cell activation, smooth muscle cell and neuroblast proliferation and bone resorption. Thrombin exerts its various biological effects through one of two mechanisms. The first is purely enzymatic, involving only the catalytic activity of thrombin. This is the mechanism by which thrombin converts fibrinogen to fibrin, the final step in the coagulation cascade.

The second mechanism of thrombin action is mediated through a cell surface receptor. This receptor has recently been cloned [T.-K. H. Vu et al., "Molecular Cloning of a Functional Thrombin Receptor Reveals a Novel Proteolytic Mechanism of Receptor Activation", *Cell*, 64 pp 1057-68 (1991)]. It is believed that thrombin activates cells via its receptor by first associating with the hirudin-like extracellular domain of the receptor (receptor amino acids 52-69) [L.-W. Liu et al., "The Region of the Thrombin Receptor Resembling Hirudin Binds to Thrombin and Alters Enzyme Specificity", *J Biol Chem.*, 266, pp. 16977-80 (1991)]. Thrombin then cleaves off a 41 amino acid peptide from its receptor's extracellularly located N-terminus, exposing a new N-terminus on the receptor. The newly exposed N-terminus then interacts with another, distant part of the receptor, resulting in activation. It is believed that activation may ultimately involve a secondary messenger, such as a kinase or cAMP, which is triggered by the cleaved receptor.

It has previously been shown that a peptide corresponding to the first 14 amino acids of the newly exposed N-terminus of the thrombin receptor (referred to as "the tethered ligand peptide") can activate the thrombin receptor in the absence of thrombin. This activation does not require the presence of an extracellular anionic domain in the receptor [T.-K. H. Vu et al., Supra].

The receptor-driven mechanism is responsible for thrombin-induced platelet aggregation and release reactions. Such reactions initiate arterial clot formation. In addition, the receptor mechanism is thought to be responsible for thrombin-induced endothelial cell activation. This activation stimulates the synthesis of platelet activating factor (PAF) in these cells [S. Prescott et al., "Human Endothelial Cells in Culture Produce Platelet-Activating Factor (1-alkyl-2-acetyl-sn-glycero-3-phosphocholine) When Stimulated With Thrombin", *Proc Natl. Acad. Sci. USA*, 81, pp. 3534-38 (1984)]. PAF is exposed on the surface of endothelial cells and serves as a ligand for neutrophil adhesion and subsequent degranulation, which results in inflammation [G. M. Vercolletti et al., "Platelet-Activating Factor Primes Neutrophil Responses to Agonists: Role in Promoting Neutrophil-Mediated Endothelial Damage", *Blood*, 71 pp. 1100-07 (1988)]. Alternatively, thrombin may promote inflammation by altering endothelial cells to produce increased vascular permeability which can lead to edema [P J. Del Vecchio et al., "Endothelial Monolayer Permeability To Macromolecules", *Fed. Proc.*, 46, pp. 2511-15 (1987)], a process that also may involve the thrombin receptor.

Smooth muscle cells are also known to express thrombin receptors on their surface [D. T. Hung et al., "Thrombin-induced Events in Non-Platelet Cells Are Mediated by the Unique Proteolytic Mechanism Established for the Cloned Platelet Thrombin Receptor, *J. Cell Biol.*, 116, pp. 827-32 (1992)]. When thrombin interacts with these cells, a proliferative response is generated. This proliferation of smooth muscle cells may contribute to restenosis following balloon angioplasty and subsequent coronary failure [A. J. B. Brady et al., "Angioplasty and Restenosis", *Brit. Med. J.*, 303, pp. 729-30 (1991)]. Other cells which have thrombin receptors are fibroblasts, neuroblasts and osteoclasts. For each of these cells, thrombin has been shown to be responsible for some bioregulatory function.

For example, thrombin has been implicated in neurodegenerative diseases because of its ability to cause neurite retraction [D. Gurwitz et al., "Thrombin Modulates and Reverses Neuroblastoma Neurite Outgrowth", *Proc Natl Acad Sci USA*, 85, pp 3440-44 (1988)]. And thrombin has been hypothesized to play a role in osteoporosis due to its ability to stimulate bone resorption by osteoclasts [D. N. Tatakis et al., "Thrombin Effects On Osteoblastic Cells -II. Structure-Function Relationships", *Biochem. Biophys. Res. Comm.*, 174, pp. 181-88 (1991)].

Therefore, the ability to regulate the in vivo activity of thrombin has many significant clinical implications. More importantly, the ability to selectively inhibit thrombin's receptor-driven functions without affecting fibrin formation is highly desirable so that bleeding will be reduced or eliminated as a potential side effect of treatment.

Compounds which inhibit thrombin directly may inhibit some or all of thrombin's functions to one degree or another. All active site inhibitors of thrombin inhibit both enzymatic and receptor-mediated functions of the molecule. Surprisingly, other thrombin inhibitors which do not bind to the active site can also inhibit both mechanisms. For example, peptides modelled on the C-terminal amino acid sequence of hirudin, a naturally occurring anticoagulant isolated from leeches, inhibit both fibrinogen cleavage, as well as thrombin-induced platelet and endothelial cell activation [U.S. patent application Ser. No. 677,609 now U.S. Pat. No. 5,256,559].

Other compounds are capable of selectively inhibiting thrombin's activities, but these compounds do not inhibit thrombin or its receptor directly and therefore are less specific. For example, heparin, which complexes with and activates antithrombin III, affects fibrin clot formation without affecting platelet-dependent thrombosis. But certain patients cannot be treated with heparin because of circulating antibodies against this compound. Also, heparin is known to cause bleeding complications. Arg-Gly-Asp-containing peptides inhibit platelet activation, without inhibiting fibrin formation. However, these peptides are general antiplatelet agents and are not specific for thrombin-induced platelet activation. These peptides work by competitively binding to the platelet surface protein, glycoprotein IIb/IIIa.

Thus, there is a great need for a direct and selective antagonist of thrombin's functions. Specifically, a compound which can inhibit thrombin's receptor-mediated functions without affecting fibrin-mediated clotting would have great utility. Such a compound would be particularly useful in preventing restenosis following angioplasty—a phenomenon linked to thrombin-induced smooth muscle cell proliferation [J. N. Wilcox, "Thrombin and Other Potential Mechanisms Underlying Restenosis", *Circulation*, 84, pp 432-35 (1991)]. Thrombin receptor antagonists would also be useful in treating or preventing arterial thrombosis without blocking fibrin formation.

SUMMARY OF THE INVENTION

The present invention solves the problems set forth above by providing novel molecules which competitively bind to and inhibit the thrombin receptor without affecting thrombin's activities toward fibrinogen and other proteins involved in coagulation. These novel antagonists are characterized by a portion which binds to the "hirudin-like" anionic domain of the thrombin receptor (amino acids 52-69). The antagonists of this invention are preferably modelled on the anion binding exosite portion of thrombin (amino acids 65-83), which is known to associate with the hirudin-like domain of its receptor.

The thrombin receptor antagonists of this invention may be utilized in compositions and methods for controlling certain thrombin-mediated functions without the risk of bleeding. This is because the molecules of this invention are specific for inhibiting thrombin receptor-mediated functions, while exerting no effect on the ability of thrombin to form fibrin clots. Pharmaceutical compositions comprising the antagonists of this invention are useful in inhibiting platelets; treating or preventing inflammation; treating or preventing bone resorption (a process prevalent in osteoporosis); treating or preventing neurodegenerative disease; and inhibiting smooth muscle cell proliferation. This last utility is particularly important following coronary angioplasty, where restenosis, which is believed to be caused by smooth muscle cell growth at the initial vessel blockage site, occurs with relatively high frequency.

Due to the fact that the antagonist molecules of the present invention may be prepared by chemical synthesis techniques, commercially feasible amounts may be produced inexpensively. Moreover, because the antagonist molecules of the present invention are significantly smaller than the thrombin inhibitors presently employed in medical treatment, they are less likely to stimulate an undesirable immune response in patients treated with them.

DETAILED DESCRIPTION OF THE INVENTION

Figure 1:
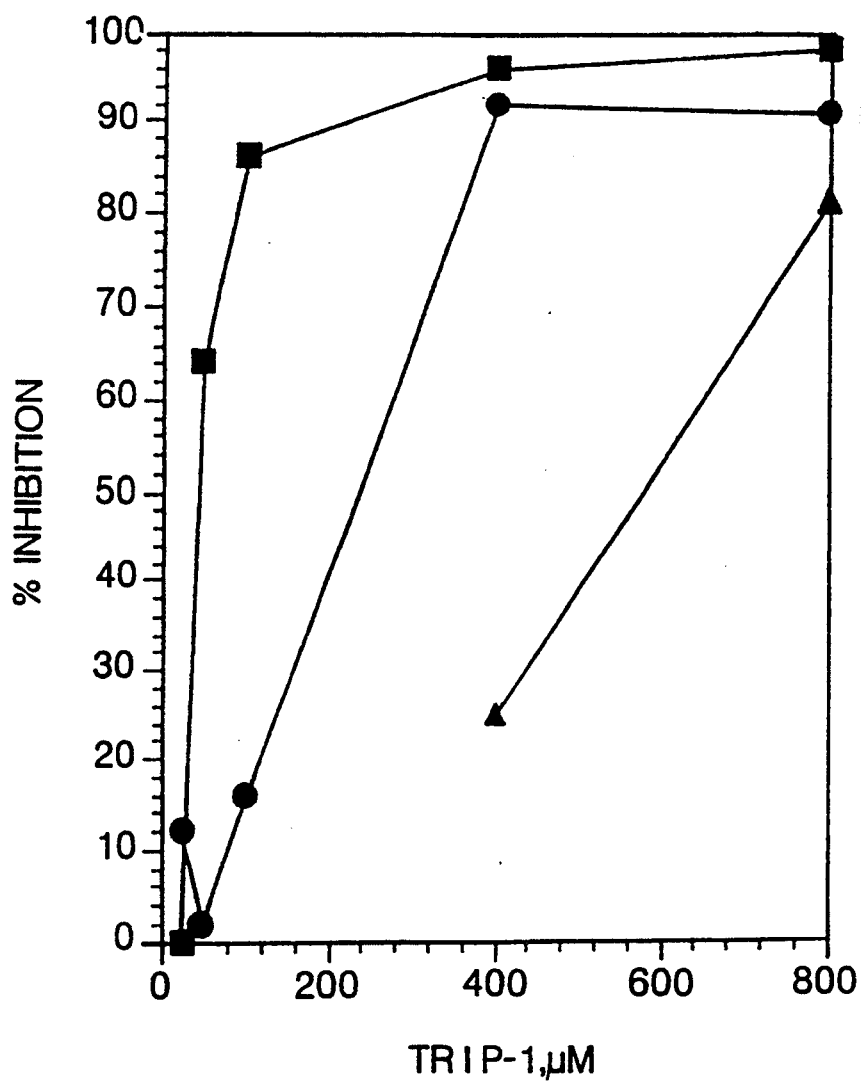
FIG. 1 depicts the inhibition of platelet aggregation by varying concentrations of TRAP-1 in the presence of varying concentrations of thrombin.

The following standard abbreviations are used throughout the specification and in the claims:

| | |
|---|---|
| Orn - ornithine | Gly - glycine |
| Ala - alanine | Val - valine |
| Leu - leucine | Ile - isoleucine |
| Pro - proline | Phe - phenylalanine |
| Trp - tryptophan | Met - methionine |
| Ser - serine | Thr - threonine |
| Cys - cysteine | Tyr - tyrosine |
| Asn - asparagine | Gln - glutamine |
| Asp - aspartic acid | Glu - glutamic acid |
| Lys - lysine | Arg - arginine |
| His - histidine | Nle - norleucine |
| Ac - acetyl | Suc - succinyl |
| BOC - tertButoxycarbonyl | Tos - paraToluenesulfonyl |
| Sar - sarcosine | CBZ - carbobenzyloxy |
| HArg - homoarginine | MPR - mercaptopropionic acid |
| GBA - guanidinobenzoic acid | PAM - phenylacetamidomethyl |
| Mts - mesitylenesulfonyl | Bzl - benzyl |
| OBzl - O-benzyl | MeBzl - methylbenzyl |
| Tyr($I_2$) - diiodotyrosine | |

The term "any amino acid" as used herein includes the L-isomers of the naturally occurring amino acids, as well as other "non-protein" α-amino acids commonly utilized by those in the peptide chemistry arts when preparing synthetic analogues of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, Y-carboxyglutamic acid, arginine, ornithine and lysine. Examples of "non-protein" α-amino acids include norleucine, norvaline, alloisoleucine, homoarginine, thioproline, dehydroproline, hydroxyproline (Hyp), isonipecotic acid (Inp), homoserine, cyclohexylglycine (Chg), α-amino-n-butyric acid (Aba), cyclohexylalanine (Cha), aminophenylbutyric acid (Pba), phenylalanines substituted at the ortho, meta, or para position of the phenyl moiety with one or two of the following: a ($C_1$–$C_4$) alkyl, a ($C_1$–$C_4$) alkoxy, halogen or nitro groups or substituted with a methylenedioxy group; β-2- and 3-thienylalalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitrotyrosine, ε-alkyl lysine, delta-alkyl ornithine, and the ε-isomers of any of the above amino acids. Unless specifically indicated, all amino acids referred to in this application are in the L-form.

The term "positively charged amino acid" as used in this application includes any naturally occurring or non-naturally occurring amino acid having a positively charged side chain. Examples of positively charged amino acids are arginine, lysine, histidine, homoarginine, ornithine and delta-alkyl ornithine.

The term "amino acid containing an aryl side chain" as used herein means any amino acid having an aromatic group. Tyrosine, phenylalanine, tryptophan, O-sulfate esters of tyrosine and 5-nitrotyrosine exemplify such amino acids.

The term "polar amino acid" means any amino acid having an uncharged side chain which is relatively soluble in water. Examples include glutamine, asparagine, glycine, serine, hydroxyproline and homoserine.

The term "hydrophobic amino acid" means any amino acid having an uncharged side chain which is relatively insoluble in water. This group includes leucine, valine, tryptophan, norleucine, norvaline, alloisoleucine, thioproline, dehydroproline, cyclohexylalanine and cyclohexylglycine.

The term "patient" as used in this application refers to any mammal, especially humans.

The term "backbone chain", as used herein, refers to the portion of a chemical structure that defines the smallest number of consecutive bonds that can be traced from one end of that chemical structure to the other. The atomic components that make up a backbone chain may comprise any atoms that are capable of forming bonds with at least two other atoms.

For example, each of the following chemical structures is characterized by a backbone chain of 7 atoms (the atoms which comprise the backbone chain are indicated in boldface):

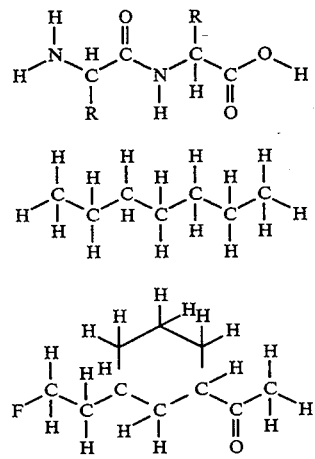

-continued

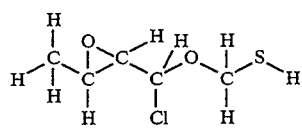

The present invention relates to molecules that compete with thrombin for binding to its cell surface receptor. This property allows the molecules of this invention to inhibit those functions of thrombin that are mediated through its receptor.

Applicant has previously shown that peptides corresponding to the C-terminal amino acid sequence of hirudin inhibit thrombin-induced platelet activation (copending U.S. patent application Ser. No. 677,609). These C-terminal hirudin peptides were known to associate with the anion binding exosite of thrombin. This work indicated that the anion binding exosite domain of thrombin was involved in platelet activation.

The recent cloning and sequencing of the platelet thrombin receptor confirmed this indication [T. -K. H. Vu et al., "Domains Specifying Thrombin-Receptor Interaction", Nature 353 pp 674–77 (1991)]. The deduced amino acid sequence of the thrombin receptor revealed the presence of a hirudin-like anionic region in an extracellular domain at amino acids 52–69. The importance of this region for thrombin's association with its receptor was demonstrated by comparing a wild-type receptor with a deletion mutant lacking that anionic region. Thrombin was 100-fold less potent in activating the mutant receptor as compared to the wild type [T.-K. H. Vu et al., supra].

By utilizing the three-dimensional X-ray crystallographic structure of a thrombin-C-terminal hirudin peptide complex [E. Skrzypczak-Jankun et al., "Structure of the Hirugen and Hirulog 1 Complexes of α-Thrombin", J. Mol. Biol., 221, pp. 1379–93 (1991)], applicant has identified some of the structural features necessary for thrombin to bind to an anionic domain. In particular, amino acids 65-83 of the thrombin β-chain form a loop at the end of two antiparallel β-strands. Many of the interactions between thrombin and the C-terminus of hirudin are mediated by side chain constituents of the loop.

By analogy, applicant believes that these side chains, which include numerous positively charged amino acids, form electrostatic complimentarity with the hirudin-like, anionic domain of the thrombin receptor. Peptides and other molecules which comprise such features will bind to the thrombin receptor and inhibit its activation by thrombin in vivo and in vitro. These peptides and other molecules, as well as compositions and methods which employ them, make up the present invention.

According to one embodiment, the thrombin receptor antagonists of the present invention are characterized by a region that binds to the "hirundin-like" domain of the thrombin receptor. Preferably, that region is modelled on the thrombin anion binding exosite (thrombin amino acids 65-83; SEQ ID NO: 1: Leu-Val-Arg-Ile-Gly-Lys-His-Ser-Arg-Thr-Arg-Tyr-Glu-Arg-Asn-Ile-Glu-Lys-Ile-Ser). The antagonists of this invention are further characterized by: (1) the ability to inhibit thrombin-induced platelet aggregation in a simple in vitro assay, and (2) the inability to inhibit platelet aggregation induced by the peptide SEQ ID NO: 2: Ser-Phe- Leu-Leu-Arg-Asn-Pro-Asn-Asp-Lys-Tyr-Glu-Pro-Phe (also referred to as "the tethered ligand of the thrombin receptor" or "the tethered ligand peptide") in a similar assay. The tethered ligand peptide corresponds to amino acids 42-55 of the thrombin receptor.

In designing an antagonist molecule according to this invention, two important considerations must be taken into account. First, the molecule must be able to physically associate with the thrombin receptor. The present theory of thrombin receptor activation suggests that the initial step in activation requires, at a minimum, an ionic interaction between the receptor and thrombin. Specifically, thrombin utilizes its anion binding exosite region, i.e., a cluster of positive charges, to bind to the anionic domain of the receptor. It is also probable that other molecular interactions, such as hydrogen bonding and hydrophobic interactions, are important for this association. Therefore, the identification and maintenance of these interactions are critical in designing a potent thrombin receptor antagonist.

The second consideration in designing the antagonists of this invention is secondary and tertiary structure. While certain portions of the antagonist do not directly participate in molecular interactions with the receptor, they may play a role in the overall conformation of the antagonist. This, in turn, can have a dramatic effect on potency. If the antagonist cannot assume the proper conformation, the molecular interactions required for association with the receptor cannot be achieved, even if the components capable of forming such interactions are present in the molecule. Accordingly, an antagonist of this invention must be designed so that it assumes a conformation which allows it to associate with the receptor. Conformational requirements may be in the nature of overall three-dimensional structure and orientation of the antagonist, or merely the spacing between two sites on the antagonist which directly interact with the receptor.

In order to identify and define the important structural and conformational attributes necessary to the thrombin receptor antagonists of this invention, one of ordinary skill in the art begins with a peptide consisting of amino acids 65-83 of thrombin. This peptide itself is a thrombin receptor antagonist of the present invention.

To test which of the 19 amino acids in this peptide are responsible for crucial molecular interactions with the thrombin receptor, a simple alanine scanning procedure is carried out. In this procedure, a series of peptides, each having a single alanine substitution at a different residue, is synthesized. The peptides are then assayed to determine if they inhibit thrombin-induced platelet aggregation, without affecting tethered peptide-induced platelet aggregation.

Those alanine-substituted peptides which retain a platelet inhibitory activity similar to that of thrombin amino acids 65-83, indicate portions of the antagonist that do not directly interact with the receptor and which do not have side chains which play a critical role in the folding of the molecule. Such peptides are preferred antagonists of the present invention. Conversely, those peptides which lack or have greatly reduced antiplatelet activity point up areas of the antagonist that are important for activity. These latter peptides suggest the nature of an important interior intramolecular interaction based upon the amino acid substituted for. For example, an arginine-to-alanine substitution which resulted in reduced activity suggests the location of an important positive charge—either an ionic interaction with the receptor or an intramolecular ionic interaction within the antagonist—which is required to maintain optimal conformation. A serine-to-alanine substitution which had a negative effect on activity indicates the location of an important hydrogen bond. Again, the hydrogen bond may be between the antagonist and the thrombin receptor, or it may be an intramolecular hydrogen bond that plays an important role in the conformation of the antagonist.

Those of skill in the art will realize that distinguishing between whether a structural feature is important for an inter- or an intramolecular interaction can only be achieved by examining an X-ray crystal structure of the antagonist-receptor complex. However, that distinction is of little import in designing the antagonists of this invention. Once the nature of the interaction is determined, i.e., electrostatic, hydrophobic, ionic, the choice of potential substitutes at that position becomes clear.

To further ascertain those sites that are important for proper folding and orientation of the thrombin receptor antagonists of this invention, a single position deletion analysis is performed. In this procedure, a series of peptides containing single deletions at positions which do not affect inhibitory activity (as determined above) are synthesized and assayed for antiplatelet activity. The peptides from this series that retain significant antiplatelet activity indicate areas of the antagonist that are not essential for proper conformation. Such peptides are also within the scope of this invention.

Deletion peptides from this series which have significantly lower platelet inhibitory activity indicate the location of components which provide critical spacing in the antagonist. This may be verified by replacing the deleted amino acid with a different, yet analogous structure. For example, substitution of any conformationally important amino acid with a three carbon alkyl chain without a significant loss of activity confirms that spacing is critical at that part of the molecule.

Additional information about important structural and conformational features necessary for designing a potent thrombin receptor antagonist of this invention may be obtained through 3-dimensional X-ray crystallographic procedures coupled with computer modelling. Specifically, one of ordinary skill in the art may analyze a thrombin receptor/thrombin amino acid 65-83 peptide complex using such a method. Alternatively, one could use the X-ray crystallographic data on the analogous C-terminal hirudin peptide-thrombin complex [E. Skrzypczak-Jankun et al., "Structure of the Hirugen and Hirulog 1 Complexes of α-Thrombin", *J. Mol. Biol.*, 221, pp. 1379-93 (1991)]. Finally, one of average skill in the art could also employ multiple alanine substitutions or multiple deletions to identify important intramolecular interactions in the antagonist itself. It will also be apparent that each new thrombin receptor antagonist designed and tested will, itself, provide additional information about structural features important for thrombin receptor inhibition.

Once the critical residues in the thrombin 65-83 peptide have been located and characterized, other thrombin receptor antagonists of this invention may be designed and synthesized. This is achieved by substituting the identified key residues of the thrombin peptide with other components having similar features. These substitutions will initially be conservative, i.e., the replacement component will have approximately the same size, shape, hydrophobicity and charge as the key residue. Those of ordinary skill in the art are well aware of appropriate replacements for a given amino acid [Dayhoff et al., in *Atlas of Protein Sequence and Structure No. 5*, 1978 and Argos et al., *EMBO J.*, 8, pp. 779-85 (1989)]. Typical conservative substitutions for an amino acid are other amino acids with similar charges. For example, aspartic acid for glutamic acid, arginine for lysine, asparagine for glutamine, hydroxyproline for proline and vice versa. Substitutions with non-natural amino acids may also be performed to reduce the peptidic nature of the antagonist. Some examples are cyclohexylalanine for tyrosine, sarcosine for glycine, statine for threonine and homoarginine for arginine. These modifications may increase the biological stability of the antagonist, in addition to increasing its potency.

After the molecule containing the substitute component is shown to be an effective thrombin receptor antagonist, less conservative replacements may be made at the same position. These substitutions typically involve the introduction of non-amino acid components which contain the important feature imparted by the amino acid at that position. Such substitutes are well-known in the art. For example, the sequence Leu-Val-Arg (corresponding to amino acids 65-67 of thrombin) can be replaced by p-guanidinobenzoic acid. This substitution maintains the hydrophobicity of Leu-Val, as well as the guanidinium functionality of Arg.

It will be apparent that there is greater freedom in selecting the substitute for a non-essential amino acid in the thrombin 65-83 amino acid sequence. Moreover, a non-essential amino acid may simply be eliminated. Almost any substitute that does not impart a change in conformation may be employed for a nonessential amino acid. These include, but are not limited to, straight chain alkyl and acyl groups. Also, because of the importance of the net positive charge of the antagonist, anionic substitutes should be avoided. Components which are known in the art to alter conformation should also be avoided. One such component is proline, an amino acid which causes a turn structure in a molecule. Others are well-known in the art [G. D. Rose et al., "Turns in Peptides and Proteins", *Adv. Prot. Chem.*, 37, pp. 1-110 (1985)].

In addition to those antagonists resulting from the substitutions and deletions described above, novel thrombin receptor antagonists according to this invention may be designed by insertions at various sites along the thrombin 65-83 peptide. To determine areas of the thrombin 65-83 peptide where a component may potentially be inserted, a series of peptides having a single alanine insertion at various sites is synthesized. Those peptides from this series which retain antiplatelet activity indicate potential insertion sites.

In choosing a component to be inserted, one should be guided by the same considerations set forth above in selecting a substitute component. Specifically, one must keep in mind how the insertions may potentially affect the molecular interactions between the antagonist and the thrombin receptor and how they affect conformation of the antagonist. For example, the insertion of an anionic component adjacent to a critical cationic amino acid in thrombin 65-83 could interfere with an important ionic interaction and should therefore be avoided. Similarly, the insertion of a component which is known to cause structural perturbations, e.g., a proline, should also be avoided.

Using any or all of the above deletion, substitution and insertion techniques allows those of ordinary skill in the art to design thrombin receptor antagonists according to this invention. Moreover, the potential effect of any of these changes may be theoretically observed prior to synthesizing the antagonist through the use of computer modelling techniques known in the art. Such modelling allows one to observe the predicted structure of a thrombin receptor complexed with the potential antagonist. If that theoretical structure suggests insufficient interaction between the receptor and the potential antagonist, one need not spend time and resources in synthesizing and testing the molecule. On the other hand, if computer modelling indicates a strong interaction, the molecule may then be synthesized and assayed for antiplatelet activity. In this manner, inoperative molecules may be eliminated before they are synthesized.

Finally, cyclic derivatives of any antagonist designed by the above techniques are also part of the present invention. Cyclization may allow the antagonist to assume a more favorable conformation for association with the thrombin receptor. Cyclization may be achieved by methods well-known to those in the art. One method is the formation of a disulfide bond between two non-adjacent cysteine residues (D- or L-conformation) or any two appropriately spaced components having free sulfhydryl groups. It will be understood that disulfide bonds, as well as other intramolecular covalent bonds, may be formed between a variety of components within the antagonist. The components which form such bonds may be side chains of amino acids, non-amino acid components or a combination of the two.

The conservative substitutions referred to antagonist of this invention which comprises the formula: SEQ ID NO: 15: $A_1$-X-X-X-$A_2$-X-$A_3$-X-$A_4$-B-X-$A_5$-C-X-$A_6$; wherein each of $A_1$ and $A_6$, either the same or different, is selected from the group consisting of a positively charged amino acid and a positively charged acyl or alkyl chain comprising from 1 to 10 backbone atoms; each of $A_2$, $A_3$, $A_4$ and $A_5$, is a positively charged amino acid, either the same or different; each X is any amino acid, either the same or different; B is an amino acid containing an aryl side chain; and C is a polar amino acid. Another preferred antagonist of this invention comprises the formula: SEQ ID NO: 16: $A_1$-X-X-X-$A_2$-X-$A_3$-X-$A_4$-B-X-$A_5$-C-X-$A_6$-$A_7$-D, wherein $A_1$, $A_2$, $A_3$, $A_4$, $A_5$, B, C and X are defined as above; each of $A_6$ and $A_7$ is a positively charged amino acid, either the same or different; and D is selected from the group consisting of a hydrophobic amino acid and a hydrophobic acyl chain of from 1 to 10 backbone atoms.

More preferred antagonists of the present invention comprise one of the two general formulae indicated above, but are characterized by specific amino acids which are present in the thrombin amino acid 65-83 sequence. These more preferred embodiments are antagonists wherein $A_1$ is Arg; antagonists wherein $A_2$ is His; antagonists wherein $A_3$ is Arg; antagonists wherein $A_4$ is Arg; antagonists wherein B is Tyr; antagonists wherein $A_5$ is Arg; antagonists wherein C is Asn; antagonists wherein $A_6$ is Glu; antagonists wherein $A_7$ is Lys; and antagonists wherein D is Ile. Even more preferred are antagonists wherein $A_3$ is Arg, B is Tyr and D is Ile.

The most preferred antagonists of the present invention are referred to as TRAPs. These antagonists have the formulae:

TRAP-I: SEQ ID NO:3: Leu-Val-Arg-Ile-Gly-Lys-His-Ser-Arg-Thr-Arg-Tyr-Glu-Arg-Asn-Ile-Glu;

TRAP-2: Leu-Val-Arg-Ile-Cys-Lys-His-Ser-Arg-Thr-Arg-Tyr-Glu-Arg-Asn-Ile-(D-Cys);

TRAP-3: SEQ ID NO:4: Leu-Cys-Arg-Ile-Gly-Lys-His-Ser-Arg-Thr-Arg-Tyr-Glu-Arg-Asn-Ile;

TRAP-4: Leu-Val-Arg-(D-Cys)-Gly-Lys-His-Ser-Arg-Thr-Arg-Tyr-Glu-Arg-Asn-Cys-Glu-Lys-Ile; and TRAP- 5: Leu-Val-Arg-(D-Cys)-Gly-Lys-His-Ser-Arg-Thr-Arg-Tyr-Glu-Arg-Asn-(D-Cys)-Glu-Lys-Ile;

TRAP- 6:
SEQ ID NO:5: Leu-Val-Arg-Ile-Gly-Lys-His-Ser-Arg-Thr-Arg-Tyr-Glu-Arg-Asn-Ile-Glu-LYs-Ile;

TRAP-7: SEQ ID NO:6: Leu-Val-Arg-Ile-Gly-Orn-His-Ser-Arg-Thr-Arg-Tyr-Glu-Arg-Asn-Ile-Glu-LYs-Ile;

TRAP-8:
SEQ ID NO:7: Leu-Val-Arg-Ile-Gly-Lys-His-Ser-Arg-Thr-Arg-Tyr-Asp-Arg-Asn-Ile-Glu-LYs-Ile;

TRAP-9: SEQ ID NO:8: Leu-Val-HArg-Ile-Gly-Lys-His-Ser-Arg-Thr-Arg-Tyr-Glu-Arg-Asn-Ile-Glu-Lys-Ile;

TRAP-10: SEQ ID NO:9: Leu-Val-Arg-Ile-Gly-Lys-His-Ser-Arg-Thr-Arg-Tyr-Glu-Arg-Asn-Ile-Glu-Lys-Cha-Gly;

TRAP-11: SEQ ID NO:10: MPR-Val-Arg-Ile-Gly-Lys-His-Ser-Arg-Thr-Arg-Tyr-Glu-Arg-Asn-Ile-Glu-Lys-Cys;

TRAP-12: SEQ ID NO:11: MPR-Cha-Val-Arg-Ile-Gly-Lys-His-Ser-Arg-Thr-Arg-Tyr-Glu-Arg-Asn-Ile-Glu-Lys-Cys;

TRAP-13: SEQ ID NO:12: Leu-Val-Arg-Ile-Gly-Lys-His-Ser-Arg-Cha-Arg-Tyr-Glu-Arg-Asn-Ile-Glu-Lys-Ile;

TRAP-14: SEQ ID NO:13: Leu-Val-Arg-Ile-Gly-Lys-His-Ser-Arg-Thr-Arg-Tyr(I2)-Glu-Arg-Asn-Ile-Glu-Lys-Ile; and TRAP-15: SEQ ID NO:14: GBA-Ile-Gly-Lys-His-Ser-Arg-Thr-Arg-Tyr-Glu-Arg-Asn-Ile-Glu-Lys-Ile.

TRAP-2, TRAP-4, TRAP-5, TRAP-11 and TRAP-12 each contains an intramolecular disulfide bond and are examples of cyclized thrombin receptor antagonists. In TRAP-2, TRAP-4 and TRAP-5, the disulfide bond is between the cysteine residues. In TRAP-11 and TRAP-12, the disulfide bond is formed between the N-terminal mercaptopropionic acid, a non-amino acid component, and the C-terminal cysteine residue.

It is known that amino acids 65-83 of thrombin form a β-loop in between two antiparallel β-strands in the naturally occurring molecule [W. Bode et al., "The Refined 1.9 Å Crystal Structure of Human α-Thrombin: Interaction With D-Phe-Pro-Arg chloromethylketone and Significance of the Tyr-Pro-Pro-Trp Insertion Segment", *EMBO J.*, 8, pp. 3467–75 (1989)]. Without being bound by theory, applicant believes that antagonists of this invention which can assume a similar conformation will be more structurally stable and therefore more potent. Thus, another embodiment of this invention is a fusion protein which comprises a thrombin receptor antagonist of this invention and which assumes such a structure.

The design of such a fusion protein initially involves identifying a naturally occurring protein which possesses a β-loop between two antiparallel β-strands structure. Several naturally occurring proteins are known to contain such a structure. These include the both heavy and light chain immunoglobulins; and serine proteases, such as trypsin. Any protein which has been crystallized can be scanned for such a loop/anti-parallel strand structure using X-ray crystallography.

Once an appropriate protein has been identified, the amino acids which make up the β-loop portion will be replaced with a peptide shown by the methods described above to act as a thrombin receptor antagonist. This replacement will normally be done at the nucleotide level by recombinant DNA technology. Because of this, the gene or a cDNA encoding the naturally occurring protein must be available. Also, the β-loop replacement i.e., the thrombin receptor antagonist peptide, must be made up entirely of naturally occurring amino acids and a synthetic gene encoding that antagonist must be synthesized.

The manipulations required to construct such a fusion protein are commonly employed in the art. Typically, this involves removing the naturally occurring β-loop coding region via restriction endonuclease digestions, exonuclease digestions or a combination of both. The remainder of the DNA encoding that protein is then isolated and ligated to a synthetic gene encoding the antagonist. Large quantities of the DNA encoding the desired fusion protein may be obtained via PCR (polymerase chain reaction) or by conventional cloning techniques. The fusion protein is subsequently produced by transformation or transfection of an appropriate host with the above DNA. Those of skill in the art are well aware of the factors necessary to achieve sufficient expression of the fusion protein. These include the operative linkage of the DNA encoding the fusion protein to an appropriate promoter, choice of appropriate host, proper growth conditions, etc.

The antiplatelet activity of the antagonists of this invention may be measured by any of a number of conventional, in vitro platelet assays. Preferably, the assay will measure a change in the degree of aggregation of platelets or a change in the release of a platelet secretory component in the presence of thrombin. The former may be measured in an aggregometer. The latter may be measured using RIA or ELISA techniques specific for the secreted component.

The ability of an antagonist of this invention to bind to the anionic domain of the thrombin receptor is easily determined in a competition assay. For example, incubation of thrombin receptor-containing cells (platelets, smooth muscle cells, endothelial cells, etc.) with a radiolabelled antagonist in the presence or absence of an unlabelled peptide corresponding to the thrombin receptor anionic domain ("thrombin receptor peptide") provides a quantification of such binding. Alternatively, affinity chromatography of the labelled antagonist on a column containing a thrombin receptor peptide cross-linked to an insoluble matrix could be used to assay binding. In this latter method, an antagonist that binds to the anionic domain of the thrombin receptor will specifically bind to the column until eluted with soluble, unlabelled thrombin receptor peptide. The above assays and methods are well-known in the art.

The thrombin receptor antagonists of the present invention may be synthesized by various techniques which are well known in the art. These include enzymatic cleavage of thrombin, recombinant DNA techniques, solid-phase peptide synthesis, solution-phase peptide synthesis, organic chemical synthesis techniques, or a combination of these techniques. The choice of synthesis technique will, of course, depend upon the composition of the particular antagonist. In a preferred embodiment of this invention, the thrombin antagonist is entirely peptidic and is synthesized by solid-phase peptide synthesis techniques, solution-phase peptide synthesis techniques or a combination thereof which constitute the most cost-efficient procedures for producing commercial quantities of these antagonists.

When "non-protein" amino acids are contained in the thrombin receptor antagonist, they may be either added directly to the growing chain during peptide synthesis or prepared by chemical modification of the complete synthesized peptide, depending on the nature of the desired "non-protein" amino acid. Those of skill in the chemical synthesis art are well aware of which "non-protein" amino acids may be added directly and which must be synthesized by chemically modifying the complete peptide chain following peptide synthesis.

The synthesis of those thrombin antagonists of this invention which contain both non-amino acid and peptidic portions is preferably achieved by a mixed heterologous/solid phase technique. This technique involves the solid-phase synthesis of all or most of the peptide portion of the molecule. This is followed by the addition of the non-amino acid components which are synthesized by solution phase techniques and then coupled to the peptidic portion via solid-phase or solution-phase methods. Any remaining peptidic portions may then be added via solid-phase or solution-phase methods.

The thrombin receptor antagonists of the present invention are useful in compositions and methods for the treatment and prophylaxis of various diseases attributed to thrombin-mediated and thrombin-associated functions and processes. These include myocardial infarction, stroke, pulmonary embolism, peripheral arterial occlusion, restenosis following arterial injury or invasive cardiological procedures, acute or chronic atherosclerosis, edema and inflammation, various cell regulatory processes (e.g. secretion, shape changes, proliferation), and neurodegenerative diseases.

The thrombin receptor antagonists of the present invention may be formulated using conventional methods to prepare pharmaceutically useful compositions, such as the addition of a pharmaceutically acceptable carrier. These compositions and the methods employing them may be used for treating or preventing platelet activation in a patient. Inhibition of thrombin-induced platelet activation is particularly useful in the treatment and prophylaxis of platelet-dependent (arterial) thrombosis.

Various dosage forms may be employed to administer the compositions of this invention. These include, but are not limited to, parenteral administration, oral administration and topical application. The compositions of this invention may be administered to the patient in any pharmaceutically acceptable dosage form, including those which may be administered to a patient intravenously as bolus or by continued infusion, intramuscularly—including paravertebrally and periarticularly—subcutaneously, intracutaneously, intra-articularly, intrasynovially, intrathecally, intra-lesionally, periostally or by oral, nasal, or topical routes. Such compositions are preferably adapted for topical, nasal, oral and parenteral administration, but, most preferably, are formulated for parenteral administration.

Parenteral compositions are most preferably administered as a constant infusion. For parenteral administration, fluid unit dose forms are prepared which contain a thrombin receptor antagonist of the present invention and a sterile vehicle. The antagonist may be either suspended or dissolved, depending on the nature of the vehicle and the nature of the particular antagonist. Parenteral compositions are normally prepared by dissolving the thrombin receptor antagonist in a vehicle, optionally together with other components, and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except that the active component is suspended rather than dissolved in the vehicle. Sterilization of the compositions is preferably achieved by exposure to ethylene oxide before suspension in the sterile vehicle. Advantageously, a surfactant or wetting agent is included in the composition to facilitate uniform distribution of its components.

Tablets and capsules for oral administration may contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents; such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate, polyethylene glycols, or acacia; non-aqueous vehicles, such as almond oil, fractionated coconut oil, and oily esters; and preservatives, such as methyl or propyl p-hydroxybenzoate or sorbic acid.

Compositions formulated for topical administration may, for example, be in aqueous jelly, oily suspension or emulsified ointment form.

The dosage and dose rate of the thrombin receptor antagonist will depend on a variety of factors, such as the size of the patient, the specific pharmaceutical composition used, the object of the treatment, i.e., therapy or prophylaxis, the nature of the condition to be treated, and the judgment of the treating physician. A pharmaceutically effective dosage is defined herein as being between about 0.001 and 100 mg/kg body weight of the patient to be treated. It should, however, be understood that other dosages may be useful based on the factors enumerated above.

Once improvement in the patient's condition has occurred, a maintenance dose of a composition of this invention is administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment upon any recurrence of disease symptoms.

According to an alternate embodiment of the present invention, the thrombin receptor antagonist may be employed in compositions and methods for inhibiting thrombin-induced smooth muscle cell proliferation in a patient. The thrombin-induced multiplication of intimal smooth muscle cells which line the outer surface of blood vessels has been implicated in advanced atherosclerosis and restenosis following angioplasty [D. T. Hung et al., *J. Cell Biol.*, 116, pp. 827–32 (1992); A. J. B. Brady et al., *Brit. J. Med.*, 303, pp. 729–30 (1991)]. The current belief is that rupture of atherosclerotic plaques—precipitated by natural causes or angioplasty—sets off a chain of events that attract thrombin to the plaque site. Once there, thrombin causes thrombus formation and smooth muscle cell proliferation. These two phenomena result in vessel blockage and potential coronary failure. Therefore, the ability to inhibit smooth muscle cell replication is of clinical importance in the ultimate success of angioplasty.

According to a preferred embodiment of the present invention, the inhibition of smooth muscle cell proliferation in a patient is achieved by inserting into said patient a device through which is conveyed a composition comprising the thrombin receptor antagonist of this invention. To allow site-specific delivery of the thrombin receptor to the intimal smooth muscle cells, a portion of the device (preferably the end) must contain aperture means which will allow the antagonist to exit the device. Such devices are well known in the art and are exemplified by balloon catheters. A preferred embodiment of this method employs a weeping balloon catheter as the device which contains the thrombin receptor antagonist composition [see for example, United States patent 5,049,132 and Wolinsky et al., "Use of a Perforated Balloon Catheter to Deliver Concentrated Heparin Into the Wall of the Normal Canine Artery", *J. Amer. Coll. Cardiol.*, 15, pp. 475–81 (1990), the disclosures of which are hereby incorporated by reference].

According to another embodiment of the present invention, thrombin receptor antagonists may be utilized in methods for treating or preventing bone resorption. Osteoclasts are the cells responsible for bone resorption in the process of turnover and remodelling of bone. These cells are known to be stimulated by thrombin through a receptor on the osteoclast cell surface [D. N. Tatakis et al., *Biochem. Biophys. Res. Comm.*, 174, pp. 181–88 (1991)]. By inhibiting thrombin-induced osteoclast activity, bone resorption is decreased. This may be specifically useful in the treatment of osteoporosis and other conditions characterized by abnormally high levels of bone resorption and demineralization.

This invention also relates to methods which employ the above-described thrombin receptor antagonists to inhibit thrombin-induced inflammation. Thrombin is known to induce the synthesis of platelet activation factor (PAF) by endothelial cells [S. Prescott et al., *Proc. Natl. Acad. Sci. USA*, 81, pp. 3534–38 (1984)]. It is believed that thrombin exerts this effect by binding to its receptor on the endothelial cell surface. These methods have important applications in the treatment of diseases characterized by thrombin-induced inflammation and edema, which are thought to be mediated be PAF. Such diseases include, but are not limited to, adult respiratory distress syndrome, septic shock, septicemia and reperfusion damage.

The thrombin receptor antagonists of this invention may also be employed in methods for treating neurodegenerative diseases. Thrombin is known to cause neurite retraction, a process suggestive of the rounding in shape changes of brain cells and implicated in neurodegenerative diseases, such as Alzheimer's disease and Parkinson's disease. It is believed that thrombin acts on neuroblasts through a specific receptor on the surface of those cells [D. Gurwitz et al., *Proc. Natl. Acad. Sci, USA*, 85, pp. 3440–44 (1988)].

In order that the invention described herein may be more fully understood, the following examples are set forth. It should be understood that these examples are for illustrative purposes only and are not to be construed as limiting this invention in any manner.

EXAMPLE 1

Synthesis Of TRAPs

Unless otherwise indicated, we synthesized all of the TRAPs by conventional solid-phase peptide synthesis using an Applied Biosystems 430 A Peptide Synthesizer (Applied Biosystems, Foster City, Calif.). The resins employed to synthesize the various TRAPs were dependent upon the C-terminal amino acid of the antagonist. Specifically, the resins used were t-BOC-L-Glu(OBzl) (OCH$_2$)-PAM, t-BOC-D-Cys(4-MeBzl) (—OCH$_2$)-PAM, t-BOC-L-Ile(OCH$_2$)-PAM, t-BOC-Gly(OCH$_2$)-PAM and t-BOC-L-Cys(4-MeBzl) (—OCH$_2$)-PAM. Resins were purchased from either Applied Biosystems or Peninsula Laboratories (Belmont, Calif.).

We employed various protected amino acids for peptide synthesis depending upon the sequence of amino acids in the particular TRAP. The protected amino acids used in the syntheses were t-BOC-L-Leu, t-BOC-L-Val, t-BOC-Arg(Mts), t-BOC-L-Ile($\frac{1}{2}$ H$_2$O), t-BOC-Gly, t-BOC-L-LyS(2-Cl-Z), t-BOC-L-Ser(Bzl), t-BOC-L-Thr(Bzl), t-BOC-L-Tyr(2-Br-z), t-BOC-L-Glu(OBzl), t-BOC-l-Asp(OBzl), t-BOC-L-Asn and t-BOC-L-Orn(2-Cl-z) from Peninsula Laboratories; and t-BOC-L-His(N-im-CBZ), t-BOC-O-(2,6-dichlorobenzyl)-3,5-diiodo-L-tyrosine and t-BOC-cyclohexyl-L-alanine from Bachem (Torrance, Calif.).

EXAMPLE 2

Synthesis Of TRAP-1

TRAP-1 (SEQ ID NO:3: Leu-Val-Arg-Ile-Gly-Lys-His-Ser-Arg-Thr-Arg-Tyr-Glu-Arg-Asn-Ile-Glu) was synthesized using t-BOC-L-Glu(OBzl)(OCH$_2$)-PAM resin and the appropriate protected amino acids selected from those listed in Example 1. After completion of synthesis, the peptide was fully deprotected and uncoupled from the resin by treatment with anhydrous HF: p-cresol: ethylmethyl sulfate (10:1:1, v/v/v). Peptides were then extracted from the resin with 5% acetic acid and lyophilized to dryness.

Crude TRAP-1 was purified by reverse-phase HPLC employing an Applied Biosystems 151A liquid chromatographic system and a Vydac C$_{18}$ column (2.2×25 cm). The column was equilibrated in 0.1% trifluoroacetic acid (TFA) in water and developed with a linear gradient of increasing acetonitrile concentration (0 to 80%) in 0.1% TFA over 45 minutes at a flow rate of 4.0 ml/min. The effluent stream was monitored at 229 nm for absorbance. Fractions were collected manually. Fractions containing TRAP-1 were pooled and lyophilized to dryness. Typically, 20–50 mg of crude TRAP-1 was loaded onto the column and yielded 5–35 mg of purified peptide.

We confirmed the structure of TRAP-1 by several techniques. Amino acid hydrolysates were prepared by treating the peptide with 6N HCl, in vacuo, at 100° C. for 24 hours. The hydrolysate was then analyzed with a Beckman 6300 amino acid analyzer (Beckman Instruments, Palo Alto, Calif.) which employs an ion-exchange separation technique coupled with post-column ninhydrin derivatization.

We performed amino acid sequence analysis using automated Edman degradation on an Applied Biosystems 470A gas-phase sequencer equipped with a Model 900A data system. Phenylthiohydantoin (PTH) amino acids were analyzed on-line using an Applied Biosystems 120A PTH-Analyzer and a PTH-$C_{18}$ column (2.1×220 mm).

We also had FAB-mass spectroscopy performed on the purified TRAP-1 by M-Scan (West Chester, Pa.), an external contract laboratory.

All of the subsequent TRAPs described below were synthesized in the same manner as that described for TRAP-1, using the appropriate resin and protected amino acids, unless otherwise indicated. Similarly, all of the below-described TRAPs were uncoupled, deprotected, purified and analyzed in the same manner as that described for TRAP-1.

EXAMPLE 3

Synthesis Of TRAP-2

TRAP-2 (Leu-Val-Arg-Ile-Cys-Lys-His-Ser-Arg-Thr-Arg-Tyr-Glu-Arg-Asn-Ile-(D-Cys)) was synthesized in the same manner as TRAP-1, using the appropriate resin and protected amino acids. Uncoupling, deprotection, purification and analysis were also performed as described for TRAP-1.

Following purification, we cyclized the antagonist by dissolving 10 mg of the peptide in 5.0 ml of 0.2 M sodium borate buffer, pH 9.0. The solution was allowed to stand at room temperature for 1–5 days. This allowed cyclization to occur by simple air oxidation of the cysteine residues.

We monitored the kinetics of cyclization by taking 50 µl aliquots of the solution at various time points. The aliquots were acidified with 50 µl of 0.1% TFA in water and then chromatographed on an Aquapore $C_8$ column (100×4.6 mm) using an Applied Biosystems 150A liquid chromatographic system. The column was developed with a linear gradient of increasing acetonitrile concentration (0–80%) in 0.1% TFA over 45 minutes. We monitored the effluent stream at 214 nm for absorbance. The presence of cyclized antagonist was indicated by the presence of a new peak of ultraviolet absorbance which eluted prior to the peak representing linear TRAP-2. We also observed additional peaks eluting after the linear TRAP-2 which were attributed to the presence of intermolecular cross-linked TRAP-2 molecules.

Cyclized TRAP-2 was purified by the same reverse-phase HPLC chromatography as described for the purification of TRAP-1. The structure of the cyclic TRAP-2 was confirmed by FAB-mass spectroscopy. The parent ion molecular mass for cyclized TRAP-2 was 2 units lower that the mass for the linear TRAP-2. This indicated that the oxidation of thiols to yield a disulfide had occurred.

All of the other cyclic TRAPs described below (TRAP-4, -5, -11 and -12) are cyclized, purified and analyzed in the same manner, unless otherwise indicated.

EXAMPLE 4

Synthesis Of TRAP-3

TRAP-3 has the formula: SEQ ID NO:4: Leu-Cys-Arg-Ile-Gly-Lys-His-Ser-Arg-Thr-Arg-Tyr-Glu-Arg-Asn-Ile and was synthesized as described above.

EXAMPLE 5

Synthesis Of TRAP-4

TRAP-4 has the formula: Leu-Val-Arg-(D-Cys)Gly-Lys-His-Ser-Arg-Thr-Arg-Tyr-Glu-Arg-Asn-Cys-Glu-Lys-Ile. TRAP-4 was synthesized and was cyclized as described above.

EXAMPLE 6

Synthesis Of TRAP-5

TRAP-5 has the formula: Leu-Val-Arg-(D-Cys)-Gly-Lys-His-Ser-Arg-Thr-Arg-Tyr-Glu-Arg-Asn-(D-Cys)-Glu-Lys-Ile. TRAP-5 was synthesized and was cyclized as described above.

EXAMPLE 7

Synthesis Of TRAP-6

TRAP-6 has the formula: SEQ ID NO:5: Leu-Val-Arg-Ile-Gly-Lys-His-Ser-Arg-Thr-Arg-Tyr-Glu-Arg-Asn-Ile-Glu-Lys-Ile and is synthesized as described above.

EXAMPLE 8

Synthesis Of TRAP-7

TRAP-7 has the formula: SEQ ID NO:6: Leu-Val-Arg-Ile-Gly-Orn-His-Ser-Arg-Thr-Arg-Tyr-Glu-Arg-Asn-Ile-Glu-Lys-Ile and is synthesized as described above.

EXAMPLE 9

Synthesis Of TRAP-8

TRAP-8 has the formula: SEQ ID NO:7: Leu-Val-Arg-Ile-Gly-Lys-His-Ser-Arg-Thr-Arg-Tyr-Asp-Arg-Asn-Ile-Glu-Lys-Ile and is synthesized as described above.

EXAMPLE 10

Synthesis Of TRAP-9

TRAP-9 has the formula: SEQ ID NO:8: Leu-Val-HArg-Ile-Gly-Lys-His-Ser-Arg-Thr-Arg-Tyr-Glu-Arg-Asn-Ile-Glu-Lys-Ile and is synthesized as described above. Boc-HArg is synthesized by conventional procedures well known in the protein synthesis art.

EXAMPLE 11

Synthesis Of TRAP-10

TRAP-10 has the formula: SEQ ID NO:9: Leu-Val-Arg-Ile-Gly-Lys-His-Ser-Arg-Thr-Arg-Tyr-Glu-Arg-Asn-Ile-Glu-Lys-Cha-Gly and is synthesized as described above.

EXAMPLE 12

Synthesis Of TRAP-11

TRAP-11 has the formula: SEQ ID NO:10: MPR-Val-Arg-Ile-Gly-Lys-His-Ser-Arg-Thr-Arg-Tyr-Glu-Arg-Asn-Ile-Glu-Lys-Cys. Residues 2–19 of this antagonist are synthesized by conventional peptide synthesis procedures as described in Example 2. The peptide resin is then reacted with a 100-fold molar excess of mercaptopropionic acid (MPR) using the conventional coupling procedure of the Applied Biosystems peptide synthesizer. The successful coupling of MPR to the antagonist is tested by ninhydrin analysis of an aliquot of the reacted resin. Absence of a blue color in the ninhydrin reaction indicates successful incorporation of MPR. If a positive reaction occurs (blue color), an additional cycle of MPR addition is performed.

Cyclization of TRAP-11 is performed as described in Example 3, following synthesis of the complete molecule.

EXAMPLE 13

Synthesis Of TRAP-12

TRAP-12 has the formula: SEQ ID NO: 11: MPR-Cha-Val-Arg-Ile-Gly-Lys-His-Ser-Arg-Thr-Arg-Tyr-Glu-Arg-Asn-Ile-Glu-Lys-Cys. TRAP-12 is synthesized in the same manner described above for TRAP-11, except that residues 2–20 are synthesized by conventional solid phase synthesis prior to MPR addition. TRAP-12 is cyclized as described above.

EXAMPLE 14

Synthesis Of TRAP-13

TRAP-13 has the formula: SEQ ID NO:12: Leu-Val-Arg-Ile-Gly-Lys-His-Ser-Arg-Cha-Arg-Tyr-Glu-Arg-Asn-Ile-Glu-Lys-Ile and is synthesized as described above.

EXAMPLE 15

Synthesis Of TRAP-14

TRAP-14 has the formula: SEQ ID NO:13: Leu-Val-Arg-Ile-Gly-Lys-His-Ser-Arg-Thr-Arg-Tyr($I_2$)-Glu-Arg-Asn-Ile-Glu-Lys-Ile and is synthesized as described above.

EXAMPLE 16

Synthesis Of TRAP-15

TRAP-15 has the formula: SEQ ID NO:14: GBA-Ile-Gly-Lys-His-Ser-Arg-Thr-Arg-Tyr-Glu-Arg-Asn-Ile-Glu-Lys-Ile. Residues 2–16 of TRAP-15 are synthesized by the conventional solid phase techniques described in Example 2. The peptide resin is then reacted with a 100-fold molar excess of para-guanidinobenzoic acid (GBA) using the conventional coupling procedure of the Applied Biosystems peptide synthesizer. Successful addition of GBA is confirmed by the ninhydrin test described for TRAP-11 (Example 12).

EXAMPLE 17

Platelet Aggregation Assays

Platelet-rich plasma (PRP) was obtained from healthy human volunteers who had refrained from taking aspirin for at least one week prior to the taking of samples. Blood was collected into 1/10 volume of 3.8% trisodium citrate using a 21 gauge butterfly cannula. The blood was then centrifuged at room temperature for 15 minutes at 100×g and the supernatant was collected. The supernatant contained 250,000–400,000 platelets/μl. We then gel-filtered the platelets by applying 20–40 ml of PRP onto a Sepharose 2B-300 column (2.5×10 cm) equilibrated and eluted with a Tyrode-HEPES buffer (129 mM NaCl, 10.9 mM trisodium citrate, 8.9 mM sodium carbonate, 5 mM HEPES, 2.8 mM KCl, 0.8 mM dibasic potassium phosphate, 0.84 mM $MgCl_2$, 0.24 mM $CaCl_2$), supplemented with 0.56 mM dextrose and 0.35% bovine serum albumin, pH 7.4. The effluent stream was monitored visually for the appearance of platelets (observed as a cloudy solution). Platelets obtained from this procedure were maintained at room temperature and used within 2 hours of preparation.

Platelet aggregation studies were performed with gel-filtered platelets using a 4-channel platelet aggregation profiler (PAP4, Biodata, Hatboro, Pa.). Specifically, the assay was performed as follows: Varying concentrations of TRAP-1, (0–1 mM final) were added to 0.45 ml of a gel-filtered platelet suspension. The mixture was then placed in the platelet aggregometer to initiate warming to 37° C. and stirring. After equilibration (approximately 5 minutes) we added human thrombin (0.16–0.48 U/ml final) to the mixture. The aggregation response was monitored for 5 minutes. Inhibition was calculated by the following formula:

$$\% \text{ inhibition} = 1 - \frac{\% \text{ aggregation in TRAP sample}}{\% \text{ aggregation in control sample}} \times 100$$

FIG. 1 demonstrates that TRAP-1 inhibited thrombin-induced platelet aggregation in a dose-dependent manner at varying thrombin concentrations. At a concentration of 800 μM, TRAP-1 inhibited thrombin-induced platelet aggregation by >80% for all concentrations of thrombin tested.

We also analyzed the ability of the thrombin receptor antagonists of this invention to inhibit platelet aggregation induced by the tethered ligand (5 μM), collagen (76 μg/ml), or ADP (4 μM). For assaying inhibition of ADP-induced platelet aggregation, the gel filtered platelet suspension is supplemented with purified human fibrinogen (1 mg/ml). For each of these assays, we used concentrations of antagonist that fully inhibited thrombin-induced aggregation (800 μM for TRAP-1). The results of this experiment are depicted in FIGS. 2 and 3.

Figure 2:
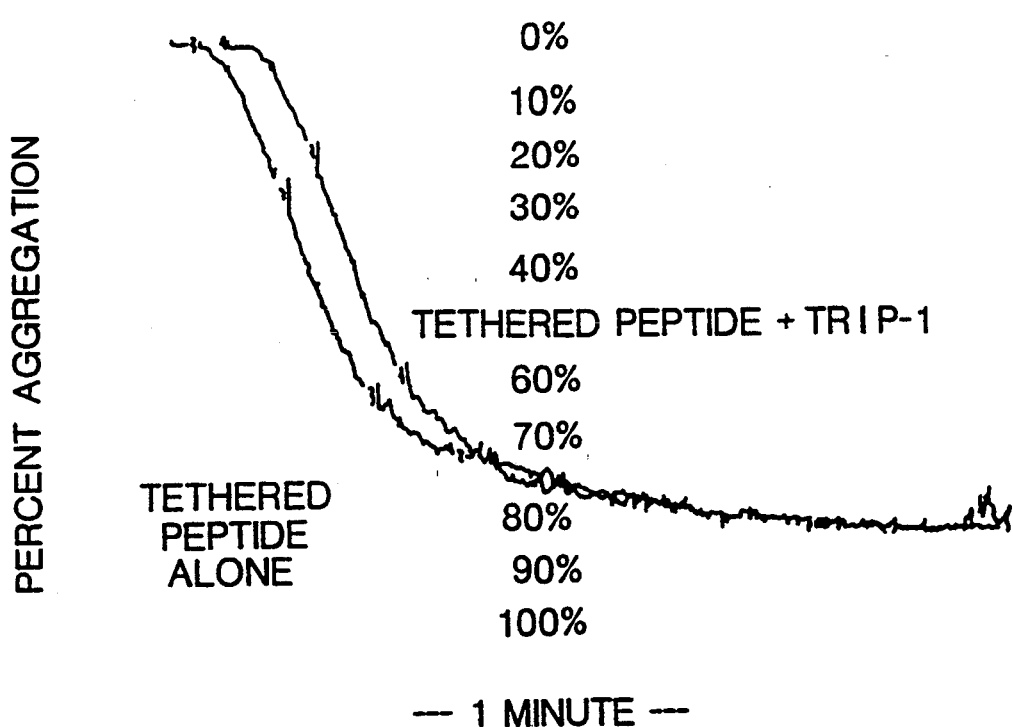
FIG. 2 depicts the lack of antiplatelet effect of TRAP-1 on platelets treated with the tethered ligand peptide of the thrombin receptor.
Figure 3:
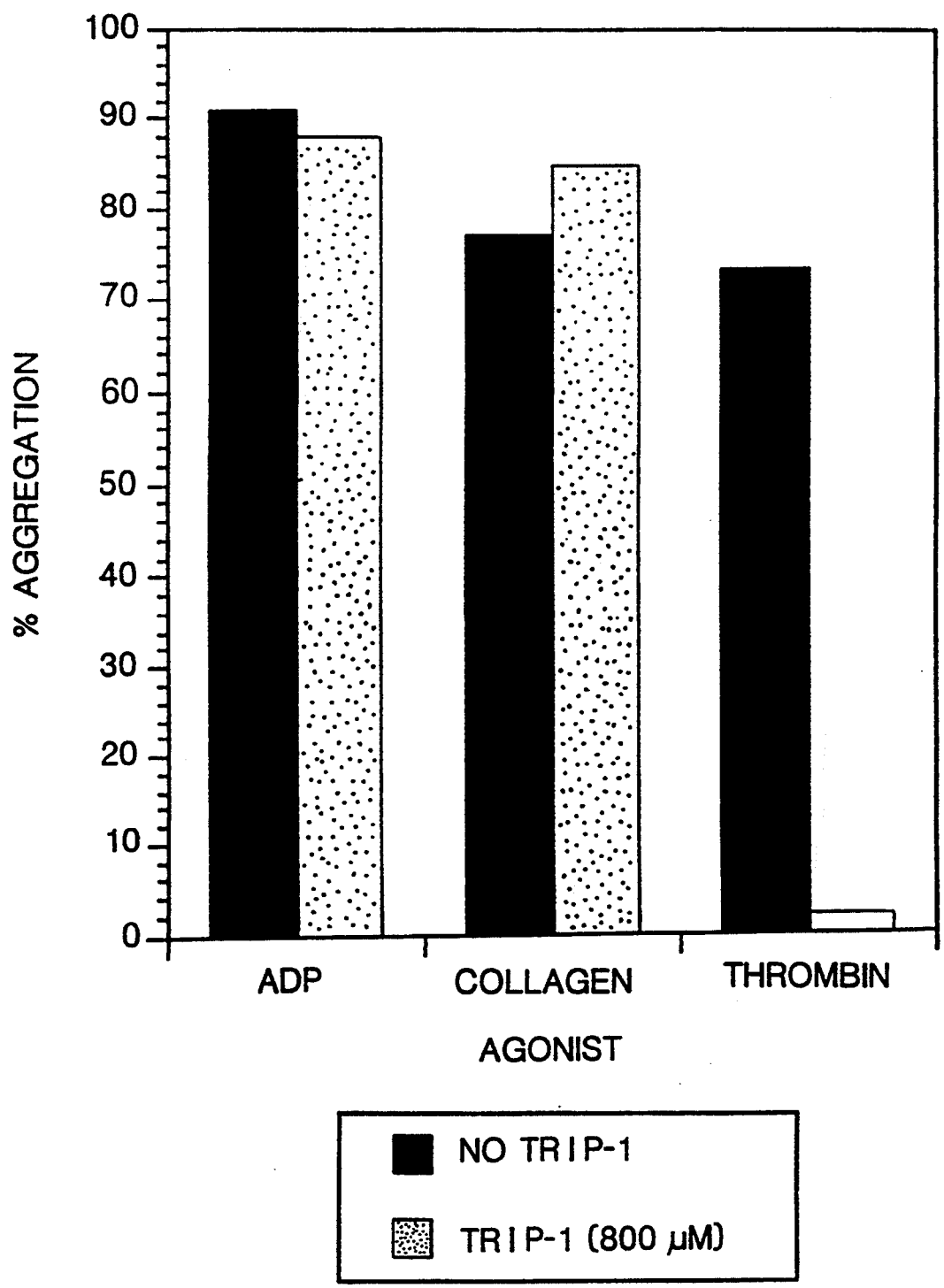
FIG. 3 depicts the efficacy of TRAP-1 in the inhibition of platelet aggregation induced by various agonists.

FIG. 2 demonstrates that TRAP-1, at a concentration which completely inhibited thrombin-induced platelet aggregation, had no inhibitory effect on platelet aggregation induced by the tethered ligand peptide. FIG. 3 shows that TRAP-1 was specific for inhibiting thrombin-induced platelet aggregation and had no effect on platelets induced by ADP or collagen.

EXAMPLE 18

Antagonist-Thrombin Receptor Binding Assays

The ability of an antagonist of this invention to bind to the hirudin-like anionic domain of the thrombin receptor is assayed by first labelling the antagonist with $^{125}I$.

The labelled antagonist is then incubated with cells containing the thrombin receptor, such as platelets or smooth muscle cells. The thrombin receptor-containing cells may be maintained in either a suspension culture or grown adherent on plastic or another suitable substrate. Binding of the antagonist to the anionic domain of the thrombin receptor is demonstrated by (1) specific binding of the labelled antagonist to the cells; and (2) significantly decreased binding of the labelled antagonist to the same cells when incubated in the presence of an unlabelled peptide corresponding to the anionic domain of the thrombin receptor (amino acids 49–62; "thrombin receptor peptide").

Alternatively, the thrombin receptor peptide may be cross-linked to an insoluble support, such as CNBr-activated Sepharose. This complex may then serve as an affinity matrix in a column for the binding of an $^{125}I$-labelled antagonist. Specific binding of an antagonist of this invention to such a matrix (and therefore to the anionic domain of the thrombin receptor) is confirmed by adsorbance to the column. The antagonist will then be specifically eluted from the column with soluble, unlabelled thrombin receptor peptide.

EXAMPLE 19

Effect Of Cyclization Of TRAP-4 And -5 On Inhibition Of Platelet Aggregation

Figure 4:
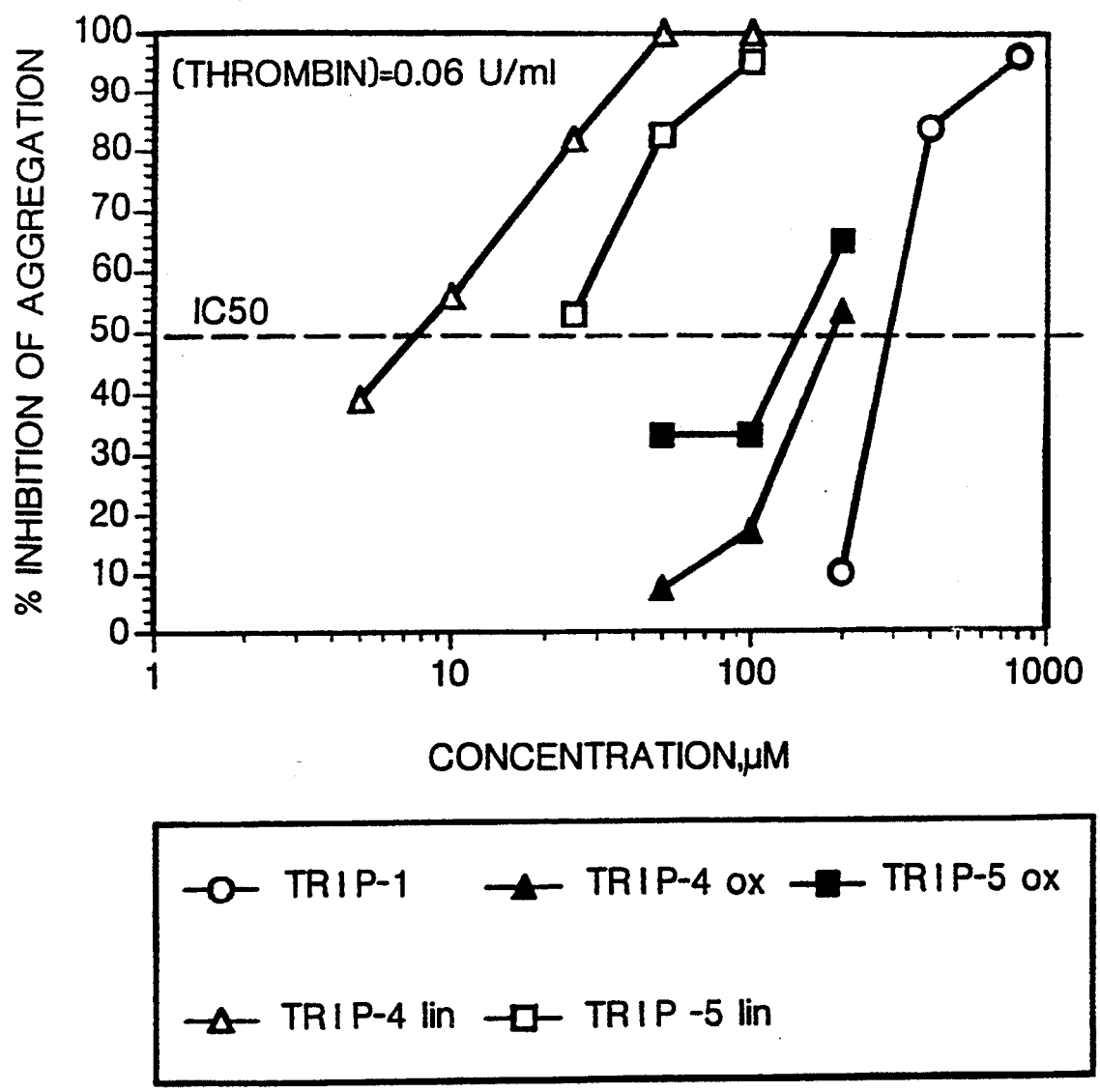
FIG. 4 depicts the comparative efficacies of TRAP-1, TRAP-4 (both linear and cyclized) and TRAP-5 (both linear and cyclized) in inhibiting thrombin-induced platelet aggregation.

We determined the effect that cyclization had on the platelet aggregation inhibitory properties of TRAP-4 and -5 in an assay similar to that described in Example 17. For this assay, we used a constant amount of thrombin (0.06 U/ml) and varying concentrations of linear or oxidized (cyclized) TRAP-4 and -5 (0-1 mM). The results were then compared to those obtained for TRAP-1 under the same conditions. FIG. 4 graphically demonstrates the results of this experiment. The table below gives the estimated $IC_{50}$ (concentration of TRAP at which 50% inhibition of platelet aggregation was achieved) values for each of these antagonists.

| Antagonist | Estimated $IC_{50}$ (μM) |
| --- | --- |
| TRAP-1 | 300 |
| TRAP-4 (linear) | 8 |
| TRAP-4 (cyclized) | 200 |
| TRAP-5 (linear) | 20 |
| TRAP-5 (cyclized) | 150 |

This table demonstrates that cyclization of TRAP-4 and -5 resulted, respectively, in a 25-fold and 7.5-fold decrease in inhibitory potency.

EXAMPLE 20

Inhibition Of Other Thrombin-Induced Cellular Functions

In general, inhibition of thrombin-induced cellular functions is assayed by pre-incubating target cells with varying concentrations of TRAP-1 (0-1 mM) for 5-30 minutes. We then add thrombin to these cells for 5-30 minutes to stimulate a given cellular response. The cells and/or media are then collected and assayed for a known thrombin-induced component. Samples incubated with TRAP-1 are compared to control samples (no TRAP-1) to quantify inhibition.

Thrombin is known to induce increased neutrophil adhesiveness in endothelial cells. To determine the inhibitory effect of TRAP-1 on this thrombin-induced function, platelet-activating factor (PAF) generation and cell surface expression of GMP-140 are analyzed [S. Prescott et al., *Proc. Natl. Acad. Sci. USA*, 81, pp. 3534-38 (1984)].

Polymorphonuclear leukocytes (PMNs) are prepared by centrifuging citrated whole blood (see Example 17) through a commercially available ficoll gradient (Pharmacia, Piscataway, N.J.). Specifically, 30 ml of whole blood is slowly pipetted down the side of the tube containing the gradient, being careful not to disturb the interface. The gradient is centrifuged for 40 minutes at 1600 rpm at 22° C. The pellet containing the PMNs is resuspended in 30 ml of white blood cell media (prepared fresh weekly) containing 25 mM HEPES, pH 7.3, with 0.5% bovine serum albumin in HBSS (without calcium and magnesium). The PMNs are then labelled for 30 minutes at 37° C. by the addition of 3.0 ml of BCECF-AM (2′,7′-bis-(2-carboxyethyl)-5(and -6)-carboxyfluorescein acetoxymethyl ester) (Molecular Probes, Inc., Eugene, Oreg.). The cells are then diluted by the addition of 5 volumes of white blood cell media.

Human umbilical vein endothelial cells (HUVECs) are grown in 48-well plates for 3 days until reaching confluency. The HUVECs are then washed with HBSS, followed by the addition of 0-1 mM TRAP-1. The cells are then incubated at 37° C. for 10-30 minutes. The PMN suspension (0.5 ml) is equilibrated to 37° C., added to HUVEC culture and allowed to settle for 2 minutes. Thrombin (0-1 U/ml) is then added to the cell mixture which is allowed to incubate for an additional 10 minutes at 37° C. The wells are washed several times with HBSS to remove non-adherent PMNs. The wells are next treated with 0.3 ml of 1% NP-40 and the contents of each well are transferred to a separate 96-well plate. Fluorescence measurements are carried out on the NP-40-treated material using an excitation wavelength of 485 nm and an emission wavelength of 538 nm. Fluorescence is proportional to the number of PMNs that adhere to the HUVEC monolayer. Pre-incubation with TRAP-1 reduces the mean fluorescence as compared to control wells containing thrombin, but no TRAP-1.

PAF generation and cell surface expression of GMP-140 are assayed as described previously [S. Prescott et al., *Proc. Natl. Acad. Sci. USA*, 81, pp. 3534-38 (1984)].

While we have hereinbefore presented a number of embodiments of this invention, it is apparent that our basic construction can be altered to provide other embodiments which utilize the processes and products of this invention. Therefore, it will be appreciated that the scope of this invention is to be defined by the claims appended hereto rather than the specific embodiments which have been presented hereinbefore by way of example.

I claim:

1. A thrombin receptor antagonist characterized by a region which binds to the anionic extracellular domain of a thrombin receptor, said antagonist consisting of the sequence: Leu-Val-Arg-X1-X2-X3-His-X4-Arg-X5-Arg-Tyr-X6-Arg-Asn-X7-Glu-Lys-Ile;
wherein:
X1 is Ile or D-Cys;
X2 is Cys or Gly;
X3 is Lys or Orn;
X4 is Ser;
X5 is Thr or Cha;
X6 is Glu or Asp; and
X7 is Cys, D-Cys or Ile.

2. The thrombin receptor antagonist according to claim 1 consisting of the sequence: Leu-Val-Arg-(D-Cys)-Gly-Lys-His-Ser-Arg-Thr-Arg-Tyr-Glu-Arg-Asn-Cys-Glu-Lys-Ile, wherein said antagonist is optionally cyclized by a disulfide bridge between the (D-Cys) residue and the Cys residue.

3. The thrombin receptor antagonist according to claim 1 consisting of the sequence: Leu-Val-Arg-(D-Cys)-Gly-Lys-His-Ser-Arg-Thr-Arg-Tyr-Glu-Arg-Asn-(D-Cys)-Glu-Lys-Ile, wherein said antagonist is optionally cyclized by a disulfide bridge between the two (D-Cys) residues.

4. The thrombin receptor antagonist according to claim 1 consisting of the sequence (SEQ ID NO:5): Leu-Val-Arg-Ile-Gly-Lys-His-Ser-Arg-Thr-Arg-Tyr-Glu-Arg-Asn-Ile-Glu-Lys-Ile.

5. The thrombin receptor antagonist according to claim 1 consisting of the sequence (SEQ ID NO:6): Leu-Val-Arg-Ile-Gly-Orn-His-Ser-Arg-Thr-Arg-Tyr-Glu-Arg-Asn-Ile-Glu-Lys-Ile.

6. The thrombin receptor antagonist according to claim 1 consisting of the sequence (SEQ ID NO:7): Leu-Val-Arg-Ile-Gly-Lys-His-Ser-Arg-Thr-Arg-Tyr-Asp-Arg-Asn-Ile-Glu-Lys-Ile.

7. The thrombin receptor antagonist according to claim 1 consisting of the sequence (SEQ ID NO:12): Leu-Val-Arg-Ile-Gly-Lys-His-Ser-Arg-Cha-Arg-Tyr-Glu-Arg-Asn-Ile-Glu-Lys-Ile.

8. A thrombin receptor antagonist consisting of the sequence: Leu-Val-Arg-Ile-Cys-Lys-His-Ser-Arg-Thr-Arg-Tyr-Glu-Arg-Asn-Ile-(D-Cys), wherein said antagonist is optionally cyclized by a disulfide bridge between the Cys residue and the (D-Cys) residue.

9. A thrombin receptor antagonist consisting of the sequence: Leu-Cys-Arg-Ile-Gly-Lys-His-Ser-Arg-Thr-Arg-Tyr-Glu-Arg-Asn-Ile.

10. A thrombin receptor antagonist consisting of the sequence (SEQ ID NO:3): Leu-Val-Arg-Ile-Gly-Lys-His-Ser-Arg-Thr-Arg-Tyr-Glu-Arg-Asn-Ile-Glu.

11. The thrombin receptor antagonist consisting of the sequence (SEQ ID NO:9): Leu-Val-Arg-Ile-Gly-Lys-His-Ser-Arg-Thr-Arg-Tyr-Glu-Arg-Asn-Ile-Glu-Lys-Cha-Gly.

12. A thrombin receptor antagonist consisting of the sequence (SEQ ID NO:10): MPR-Val-Arg-Ile-Gly-Lys-His-Ser-Arg-Thr-Arg-Tyr-Glu-Arg-Asn-Ile-Glu-Lys-Cys, wherein said antagonist is optionally cyclized by a disulfide bridge between MPR and the Cys residue.

13. A thrombin receptor antagonist consisting of the sequence (SEQ ID NO:11): MPR-Cha-Val-Arg-Ile-Gly-Lys-His-Ser-Arg-Thr-Arg-Tyr-Glu-Arg-Asn-Ile-Glu-Lys-Cys, wherein said antagonist is optionally cyclized by a disulfide bridge between MPR and the Cys residue.

14. A composition comprising an amount of a thrombin receptor antagonist as in any one of claims 1–9 effective to inhibit thrombin from binding to its receptor and a pharmaceutically acceptable carrier.

* * * * *